US00RE47646E

(19) United States
(12) Reissued Patent
Rice et al.

(10) Patent Number: US RE47,646 E
(45) Date of Reissued Patent: Oct. 15, 2019

(54) METHOD AND ASSOCIATED INSTRUMENTATION FOR INSTALLATION OF SPINAL DYNAMIC STABILIZATION SYSTEM

(71) Applicant: Zimmer Spine, Inc., Edina, MN (US)

(72) Inventors: Mark W. Rice, Minneapolis, MN (US); Thomas J Gisel, Chaska, MN (US); Hugh D Hestad, Edina, MN (US); Mark J Kroll, St. Paul, MN (US)

(73) Assignee: Zimmer Spine, Inc., Edina, MN (US)

(21) Appl. No.: 15/619,948

(22) Filed: Jun. 12, 2017

Related U.S. Patent Documents

Reissue of:
(64) Patent No.: 8,632,572
Issued: Jan. 21, 2014
Appl. No.: 13/048,447
Filed: Mar. 15, 2011

U.S. Applications:
(60) Division of application No. 14/995,435, filed on Jan. 14, 2016, now Pat. No. Re. 47,377, which is an application for the reissue of Pat. No. 8,632,572, which is a continuation of application No. 11/737,151, filed on Apr. 19, 2007, now Pat. No. 7,922,725.

(51) Int. Cl.
*A61B 17/56* (2006.01)
*A61B 17/88* (2006.01)

(52) U.S. Cl.
CPC ..... *A61B 17/56* (2013.01); *A61B 17/88* (2013.01); *A61B 2017/564* (2013.01)

(58) Field of Classification Search
CPC ..... A61B 17/7083; A61B 17/7085
USPC ..... 606/279, 86 A, 263, 270
See application file for complete search history.

(56) References Cited

U.S. PATENT DOCUMENTS

| | | | |
|---|---|---|---|
| 2,248,054 | A | 7/1941 | Joseph |
| 4,526,067 | A | 7/1985 | Gaquere |
| 4,862,774 | A | 9/1989 | Else |
| 4,946,458 | A | 8/1990 | Harms |
| 5,030,220 | A | 7/1991 | Howland |

(Continued)

FOREIGN PATENT DOCUMENTS

| | | |
|---|---|---|
| CA | 2684238 A1 | 10/2008 |
| DE | 602008037791 | 4/2015 |

(Continued)

OTHER PUBLICATIONS

Zimmer Spine, Dynesys LIS Less Invasive Surgery, The Dynamic Stabilization System, copyright 2005.*

(Continued)

*Primary Examiner* — Beverly M Flanagan
(74) *Attorney, Agent, or Firm* — Schwegman Lundberg & Woessner, P.A.

(57) ABSTRACT

In one embodiment, a spinal stabilization apparatus includes a vertebral anchor having a head portion and a bone attachment portion. An elongate, flexible guide is removably coupled to the head portion of the vertebral anchor and has a channel extending longitudinally thereof and communicating with a slot in the head portion of the anchor. An elongate cord may be received within the channel to facilitate inserting and securing a spacer between pairs of anchors installed into adjacent vertebrae of a person's spine.

6 Claims, 6 Drawing Sheets

(56) References Cited

U.S. PATENT DOCUMENTS

| | | | |
|---|---|---|---|
| 5,261,913 | A | 11/1993 | Marnay |
| 5,360,431 | A | 11/1994 | Puno et al. |
| 5,458,030 | A | 10/1995 | Betts et al. |
| 5,540,688 | A | 7/1996 | Navas |
| 5,562,660 | A | 10/1996 | Grob |
| 5,584,831 | A | 12/1996 | McKay |
| 5,672,176 | A | 9/1997 | Biedermann |
| 5,681,319 | A | 10/1997 | Biedermann |
| 5,989,254 | A | 11/1999 | Katz |
| 6,112,623 | A | 9/2000 | Bigand et al. |
| 6,139,549 | A | 10/2000 | Keller |
| 6,183,472 | B1 | 2/2001 | Lutz |
| 6,290,700 | B1 | 9/2001 | Schmotzer |
| 6,391,030 | B1 | 5/2002 | Wagner et al. |
| 6,402,752 | B2 | 6/2002 | Schaffler-Wachter |
| 6,471,705 | B1 | 10/2002 | Biedermann |
| 6,530,929 | B1 | 3/2003 | Justis et al. |
| 6,616,667 | B1 | 9/2003 | Steiger et al. |
| 6,695,843 | B2 | 2/2004 | Biedermann |
| 6,723,100 | B2 | 4/2004 | Biedermann |
| 6,736,820 | B2 | 5/2004 | Biedermann |
| 6,835,196 | B2 | 12/2004 | Biedermann |
| 6,896,677 | B1 | 5/2005 | Lin |
| 6,905,500 | B2 | 6/2005 | Jeon et al. |
| 6,918,911 | B2 | 7/2005 | Biedermann |
| 6,932,822 | B2 | 8/2005 | Oribe et al. |
| 6,986,771 | B2 | 1/2006 | Paul |
| 6,989,011 | B2 | 1/2006 | Paul |
| 6,994,710 | B2 | 2/2006 | White et al. |
| 7,008,424 | B2 | 3/2006 | Teitelbaum |
| 7,018,378 | B2 | 3/2006 | Biedermann et al. |
| 7,073,415 | B2 | 7/2006 | Casutt et al. |
| 7,081,116 | B1 | 7/2006 | Carly |
| 7,090,679 | B2 | 8/2006 | Saint-Martin et al. |
| 7,250,052 | B2 | 7/2007 | Landry et al. |
| 7,326,210 | B2 | 2/2008 | Jahng et al. |
| 7,476,240 | B2 | 1/2009 | Raymond et al. |
| 7,758,584 | B2 | 7/2010 | Bankoski et al. |
| 7,918,857 | B2 | 4/2011 | Dziedzic et al. |
| 7,918,858 | B2 | 4/2011 | Stad et al. |
| 7,922,725 | B2 | 4/2011 | Darst Rice et al. |
| 7,927,360 | B2 | 4/2011 | Pond, Jr. et al. |
| 8,632,572 | B2 | 1/2014 | Darst Rice et al. |
| 2001/0007074 | A1 | 7/2001 | Strobel et al. |
| 2001/0012937 | A1 | 8/2001 | Schaffler-Wachter |
| 2002/0035366 | A1 | 3/2002 | Walder |
| 2002/0058942 | A1 | 5/2002 | Biedermann |
| 2002/0082602 | A1 | 6/2002 | Biedermann |
| 2002/0116001 | A1 | 8/2002 | Schafer |
| 2002/0133154 | A1 | 9/2002 | Saint Martin |
| 2002/0133159 | A1 | 9/2002 | Jackson |
| 2002/0138076 | A1 | 9/2002 | Biedermann et al. |
| 2002/0143341 | A1 | 10/2002 | Biedermann |
| 2002/0161368 | A1 | 10/2002 | Foley et al. |
| 2003/0018342 | A1 | 1/2003 | Oribe et al. |
| 2003/0023243 | A1 | 1/2003 | Biedermann |
| 2003/0100896 | A1 | 5/2003 | Biedermann |
| 2003/0100904 | A1 | 5/2003 | Biedermann |
| 2003/0114860 | A1 | 6/2003 | Cavagna et al. |
| 2003/0125741 | A1 | 7/2003 | Biedermann |
| 2003/0187439 | A1 | 10/2003 | Biedermann |
| 2004/0097933 | A1 | 5/2004 | Lourdel et al. |
| 2004/0102781 | A1 | 5/2004 | Jeon |
| 2004/0122425 | A1 | 6/2004 | Suzuki et al. |
| 2004/0138662 | A1 | 7/2004 | Landry et al. |
| 2004/0143265 | A1 | 7/2004 | Landry et al. |
| 2004/0153077 | A1 | 8/2004 | Biedermann |
| 2004/0176766 | A1 | 9/2004 | Shluzas |
| 2004/0181224 | A1 | 9/2004 | Biedermann |
| 2004/0186474 | A1 | 9/2004 | Matthis et al. |
| 2004/0225289 | A1 | 11/2004 | Biedermann et al. |
| 2004/0243193 | A1 | 12/2004 | Ballis |
| 2004/0249378 | A1 | 12/2004 | Saint Martin et al. |
| 2005/0010220 | A1 | 1/2005 | Casutt et al. |
| 2005/0055026 | A1 | 3/2005 | Biedermann et al. |
| 2005/0065516 | A1 | 3/2005 | Jahng |
| 2005/0065526 | A1 | 3/2005 | Drew et al. |
| 2005/0085815 | A1 | 4/2005 | Harms et al. |
| 2005/0124991 | A1 | 6/2005 | Jahng |
| 2005/0131408 | A1 | 6/2005 | Sievol et al. |
| 2005/0131410 | A1 | 6/2005 | Lin |
| 2005/0131421 | A1 | 6/2005 | Anderson et al. |
| 2005/0143737 | A1 | 6/2005 | Pafford et al. |
| 2005/0154389 | A1 | 7/2005 | Selover et al. |
| 2005/0154390 | A1 | 7/2005 | Biedermann et al. |
| 2005/0171542 | A1 | 8/2005 | Biedermann |
| 2005/0192570 | A1 | 9/2005 | Jackson |
| 2005/0192579 | A1 | 9/2005 | Jackson |
| 2005/0203513 | A1 | 9/2005 | Jahng et al. |
| 2005/0234451 | A1 | 10/2005 | Markworth |
| 2005/0267472 | A1 | 12/2005 | Biedermann |
| 2006/0036255 | A1 | 2/2006 | Pond, Jr. et al. |
| 2006/0084993 | A1 | 4/2006 | Landry et al. |
| 2006/0084995 | A1 | 4/2006 | Biedermann |
| 2006/0106383 | A1 | 5/2006 | Biedermann |
| 2006/0111712 | A1 | 5/2006 | Jackson |
| 2006/0111713 | A1 | 5/2006 | Jackson |
| 2006/0111715 | A1 | 5/2006 | Jackson |
| 2006/0142758 | A1 | 6/2006 | Petit |
| 2006/0142761 | A1 | 6/2006 | Landry et al. |
| 2006/0155277 | A1 | 7/2006 | Metz-Stavenhagen |
| 2006/0200132 | A1 | 9/2006 | Chao et al. |
| 2006/0217738 | A1 | 9/2006 | Tanimura |
| 2006/0230887 | A1 | 10/2006 | Taguchi |
| 2007/0016200 | A1 | 1/2007 | Jackson |
| 2007/0055244 | A1 | 3/2007 | Jackson |
| 2007/0078461 | A1 | 4/2007 | Shluzas |
| 2007/0129729 | A1 | 6/2007 | Petit |
| 2007/0198088 | A1 | 8/2007 | Biedermann et al. |
| 2007/0270860 | A1 | 11/2007 | Jackson |
| 2007/0293862 | A1 | 12/2007 | Jackson |
| 2008/0009863 | A1 | 1/2008 | Bond et al. |
| 2008/0051787 | A1* | 2/2008 | Remington ..... A61B 17/7005 606/279 |
| 2008/0091213 | A1 | 4/2008 | Jackson |
| 2008/0140076 | A1 | 6/2008 | Jackson |
| 2008/0147122 | A1 | 6/2008 | Jackson |
| 2008/0177317 | A1 | 7/2008 | Jackson |
| 2008/0183216 | A1 | 7/2008 | Jackson |
| 2008/0262551 | A1 | 10/2008 | Rice et al. |
| 2011/0166604 | A1 | 7/2011 | Darst Rice et al. |

FOREIGN PATENT DOCUMENTS

| | | | |
|---|---|---|---|
| EP | 0669109 | A | 8/1995 |
| EP | 0669109 | B1 | 5/1999 |
| EP | 1523949 | A1 | 4/2005 |
| EP | 1523949 | B1 | 6/2007 |
| EP | 2152179 | B1 | 2/2010 |
| EP | 2152179 | | 4/2015 |
| FR | 2715057 | A1 | 7/1995 |
| FR | 2715057 | B1 | 3/1996 |
| FR | 2844180 | A1 | 3/2004 |
| FR | 2844180 | B1 | 8/2005 |
| FR | 2867057 | A1 | 9/2005 |
| FR | 2867057 | B1 | 6/2007 |
| NL | 7610576 | A | 3/1978 |
| WO | WO-8900028 | A1 | 1/1989 |
| WO | WO-9000377 | A1 | 1/1990 |
| WO | WO-9106254 | A1 | 5/1991 |
| WO | WO-9116020 | A1 | 10/1991 |
| WO | WO-9220294 | A1 | 11/1992 |
| WO | WO-9311715 | A1 | 6/1993 |
| WO | WO-9414384 | A2 | 7/1994 |
| WO | 9414384 | A3 | 8/1994 |
| WO | 9417745 | A1 | 8/1994 |
| WO | WO-9414384 | A3 | 8/1994 |
| WO | WO-9417745 | A1 | 8/1994 |
| WO | WO-9501132 | A1 | 1/1995 |
| WO | WO-9513755 | A1 | 5/1995 |
| WO | WO-9513756 | A1 | 5/1995 |
| WO | WO-9514437 | A1 | 6/1995 |
| WO | WO-9519149 | A1 | 7/1995 |
| WO | WO-9812977 | A1 | 4/1998 |

(56) References Cited

FOREIGN PATENT DOCUMENTS

| | | | |
|---|---|---|---|
| WO | WO-9905980 | A1 | 2/1999 |
| WO | WO-0027297 | A1 | 5/2000 |
| WO | WO-0101873 | A1 | 1/2001 |
| WO | WO-02069854 | A1 | 9/2002 |
| WO | WO-2004004549 | A2 | 1/2004 |
| WO | WO-2004024011 | A1 | 3/2004 |
| WO | WO-2004041100 | A1 | 5/2004 |
| WO | 2004004549 | A8 | 3/2005 |
| WO | WO-2005087121 | A1 | 9/2005 |
| WO | WO-2006066685 | A1 | 6/2006 |
| WO | WO-2008130728 | | 10/2008 |

OTHER PUBLICATIONS

"U.S. Appl. No. 14/995,435, Examiner Interview Summary dated 'Dec. 22, 2016", 3 pgs.
"U.S. Appl. No. 14/995,435, Non Final Office Action dated Mar. 13, 2017", 17 pgs.
"U.S. Appl. No. 14/995,435, Non Final Office Action dated Jul. 11, 2016", 15 pgs.
"U.S. Appl. No. 14/995,435, Response filed Dec. 12, 2016 to Non Final Office Action dated Jul. 11, 2016", 12 pgs.
"U.S. Appl. No. 14/995,435, Non Final Office Action dated Sep. 26, 2017", 17 pgs.
"U.S. Appl. No. 4/995,435, Preliminary Amendment filed Jan. 14, 2016", 8 pgs.
"U.S. Appl. No. 14/995,435, Response filed Jun. 13, 2017 to Non Final Office Action dated Mar. 13, 2017", 13 pgs.
"U.S. Appl. No. 11/737,151, Non Final Office Action dated Aug. 17, 2010", 13 pgs.
"U.S. Appl. No. 11/737,151, Notice of Allowance dated Dec. 3, 2010", 4 pgs.
"U.S. Appl. No. 11/737,151, Response filed Nov. 17, 2010 to Non Final Office Action dated Aug. 17, 2010", 11 pgs.
"U.S. Appl. No. 13/048,447, Final Office Action dated Jul. 10, 2013", 8 pgs.
"U.S. Appl. No. 13/048,447, Non Final Office Action dated Mar. 25, 2013", 8 pgs.
"U.S. Appl. No. 13/048,447, Notice of Allowance dated Sep. 16, 2013", 6 pgs.
"U.S. Appl. No. 13/048,447, Response filed Jun. 25, 2013 to Non Final Office Action dated Mar. 25, 2013", 10 pgs.
"U.S. Appl. No. 13/048,447, Response filed Sep. 6, 2013 to Final Office Action dated Jul. 10, 2013", 4 pgs.
"U.S. Appl. No. 14/995,435, Non Final Office Action dated Mar. 14, 2018", 15 pgs.
"U.S. Appl. No. 14/995,435, Response filed Dec. 22, 2017 to Non Final Office Action dated Sep. 26, 2017", 14 pgs.
"U.S. Appl. No. 14/995,435, Response filed Jul. 13, 2018 to Non Final Office Action dated Mar. 14, 2018", 15 pgs.
"Canadian Application Serial No. 2,684,238, Voluntary Amendment filed Oct. 15, 2009", 5 pgs.
"European Application Serial No. 08728645.6, Communication Pursuant to Article 94(3) EPC dated Jan. 27, 2014", 4 pgs.
"European Application Serial No. 08728645.6, Communication Pursuant to Article 94(3) EPC dated Mar. 7, 2013", 5 pgs.
"European Application Serial No. 08728645.6, Decision to grant dated Mar. 26, 2015", 2 pgs.
"European Application Serial No. 08728645.6, Extended European Search Report dated Jul. 10, 2012", 8 pgs.
"European Application Serial No. 08728645.6, Intention to Grant dated Nov. 5, 2014", 35 pgs.
"European Application Serial No. 08728645.6, Response filed Feb. 5, 2013 to Extended European Search Report dated Jul. 10, 2012", 23 pgs.
"European Application Serial No. 08728645.6, Response filed Jun. 5, 2014 to Communication Pursuant to Article 94(3) EPC dated Jan. 27, 2014", 11 pgs.
"European Application Serial No. 08728645.6, Response filed Jul. 16, 2013 to Communication Pursuant to Article 94(3) EPC dated Mar. 7, 2013", 12 pgs.
"International Application Serial No. PCT/US2008/052576, International Preliminary Report on Patentability dated Oct. 20, 2009", 6 pgs.
"International Application Serial No. PCT/US2008/052576, International Search Report dated Jul. 28, 2008", 1 page.
"International Application Serial No. PCT/US2008/052576, Written Opinion dated Jul. 28, 2008", 5 pgs.
Davis, Reginald J, et al., "Dynesys LIS surgical technique", Dynesys LIS Less Invasive Surgery, The Dynamic Stabilization System, (2005), 24 pgs.

* cited by examiner

METHOD AND ASSOCIATED INSTRUMENTATION FOR INSTALLATION OF SPINAL DYNAMIC STABILIZATION SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

REFERENCE TO RELATED APPLICATIONS

[This application] *The present application is a reissue divisional of U.S. patent application Ser. No. 14/995,435, filed on Jan. 14, 2016, which is also a reissue of U.S. Pat. No. 8,632,572. U.S. Pat. No. 8,632,572* is a continuation of U.S. patent application Ser. No. 11/737,151, filed Apr. 19, 2007, now U.S. Pat. No. 7,922,725 B2[, which is incorporated herein by reference].

TECHNICAL FIELD

This invention relates generally to spinal support devices, and more particularly to methods and devices that facilitate installing an implantable system for providing dynamic stability of a person's spine.

BACKGROUND OF THE INVENTION

The treatment of acute and chronic spinal instabilities or deformities of the thoracic, lumbar, and sacral spine has traditionally involved the implantation of rigid rods to secure the vertebrae of a patient. More recently, flexible materials have been utilized in connection with securing elements, such as pedicle screws, to provide a dynamic stabilization of the spine. Such dynamic stabilization systems typically include a flexible spacer positioned between pedicle screws installed in adjacent vertebrae of a person's spine. Once the spacer is positioned between the pedicle screws, a flexible cord is threaded through eyelets formed in the pedicle screws and an aperture through the spacer. The flexible cord retains the spacer between the pedicle screws while cooperating with the spacer to permit mobility of the spine. Traditional implantation of such dynamic stabilization systems may require relatively large surgical sites to permit threading the cord through the screws and spacer once the spacer has been positioned between the screws.

While some dynamic stabilization systems have been proposed for permitting the top loading of a spacer and cord between pedicle screws, these systems also require added instrumentation and procedures to distract the pedicle screws for placement of the spacer.

A need therefore exists for a spinal dynamic stabilization system and associated installation tools and techniques that overcome these and other drawbacks of the prior art.

SUMMARY OF THE INVENTION

This invention overcomes the foregoing and other shortcomings and drawbacks of spinal stabilization systems heretofore known for use in suitable various commercial and industrial environments. While various embodiments will be described herein, the invention is not limited to these embodiments. On the contrary, the invention includes all alternatives, modifications and equivalents as may be included within the spirit and scope of this invention.

In one embodiment, a system for stabilizing a patient's spine includes a pair of vertebral anchors adapted to be anchored to first and second vertebrae, respectively. Each vertebral anchor has an upwardly open channel. A connecting element that may be in the form of a flexible cord extends between the vertebral anchors and is seated in the channels. An annular spacer is positioned between the channels of the vertebral anchors with the connecting element passing there through. A pair of fasteners is each mated with the one of the channels of the vertebral anchors to secure the connecting element thereto. A pair of access members in the form of sleeves is mounted on the vertebral anchors and each sleeve has a cannula to provide percutaneous access to the vertebral anchor when mounted thereon.

A slot in each of the sleeves is in communication with the associated channel when mounted on the vertebral anchor. The system includes one tool having a tubular member with a cannula extending there through and configured to fit over one of the sleeves when mounted on the associated vertebral anchor. The tool is used by the surgeon to advance the connecting member along the slot and into the channel of one of the vertebral anchors and to position the spacer between the vertebral anchors. In alternative embodiments, the tool may have an arcuate flange on its distal end to cradle the spacer for distraction during insertion between the vertebral anchors.

The system may include another tool also having a tubular member with a cannula extending there through and configured to fit over one of the sleeves when mounted on the associated vertebral anchor. This tool is adapted to advance the connecting member along the slot and into the channel of the vertebral anchors. This tool may include a mating feature proximate the distal end and complementary to a mating feature on either the vertebral anchor or the sleeve to thereby couple the tool thereto. The complementary mating features may include a recess on the distal end of the tool, a recess on the head of the pedicle screw, an outwardly directed protrusion proximate a distal end of the sleeve, and an inwardly directed protrusion proximate the distal end of the sleeve. The recesses are configured to mate with the protrusions to releasably secure the tool to the pedicle screw and allow the surgeon to use the tool to screw the pedicle screws into the vertebrae.

Other embodiments of this invention involve the installation procedures for a spinal stabilization construct and include installing the vertebral anchors onto the vertebrae and mounting access members, which in one embodiment are sleeves, onto the vertebral anchors. Each sleeve has a cannula to provide percutaneous access to the channel of the respective vertebral anchor. The connecting element is inserted through a slot in one of the sleeves and is advanced from the slot into the channel in the associated vertebral anchor. The connecting element is secured to the channel of the vertebral anchor with a fastener and an annular spacer is positioned on the connecting element adjacent the vertebral anchor.

The connecting element is inserted through a slot in the other sleeve and advanced into the channel in the second vertebral anchor. The spacer distracts against the first vertebral anchor and positions the spacer between the vertebral anchors. The connecting element is secured to the channel of the second vertebral anchor with a second fastener. The connecting element may be a flexible cord that is tensioned between the vertebral anchors. The respective fasteners may be passed through the sleeves percutaneously to the respective channels in conjunction with the tensioning of the cord or connecting element.

These and other features, objects and advantages of the invention will become more readily apparent to those skilled in the art in view of the following detailed description, taken in conjunction with the accompanying drawings.

BRIEF DESCRIPTION OF THE DRAWINGS

The accompanying drawings, which are incorporated in and constitute a part of this specification, illustrate embodiments of the invention and, together with the general description of the invention given above, and the detailed description given below, serve to explain the principles of the invention.

DETAILED DESCRIPTION

Figure 1:
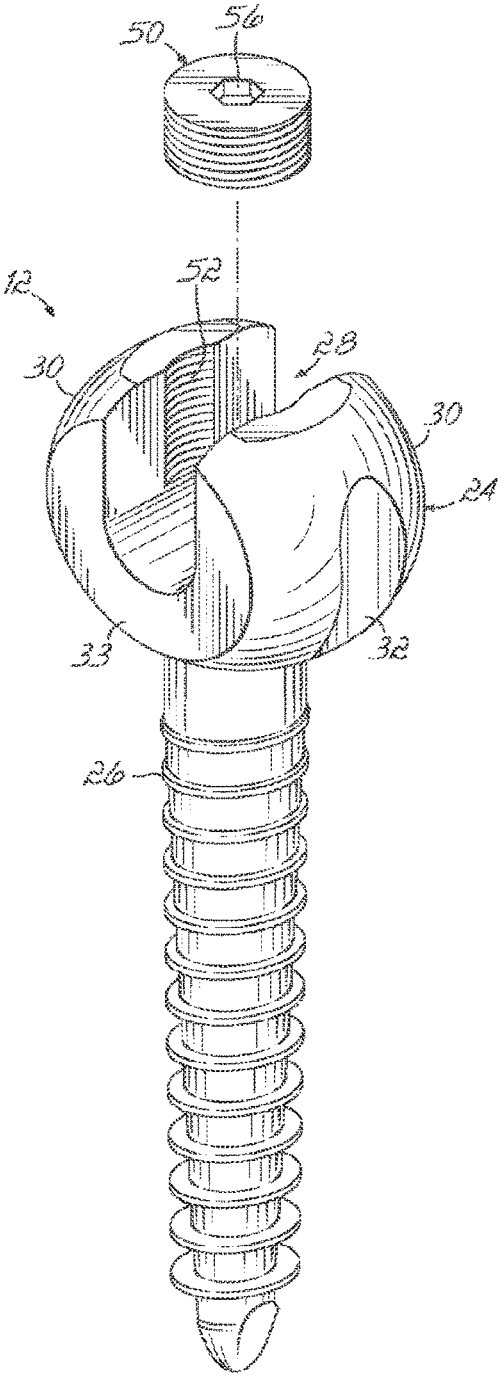
FIG. 1 is a perspective view of a vertebral anchor in the form of a pedicle screw and an associated fastener in the form of a set screw according to one aspect of this invention.

FIGS. 1-2 and 6-7 depict some of the components of one embodiment of a spinal stabilization system 10 according to this invention. Specifically, vertebral anchors 12 are adapted to be installed into adjacent vertebrae 14,16 of the spine using removable access members 18 inserted through an incision formed through the patient's skin. The incision may be sized for minimally invasive percutaneous or retractor based techniques or may be used in open procedures. In the embodiment shown, at least two anchors 12, shown here in the form of pedicle screws, are fixedly installed into the pedicle area of adjacent vertebrae 14,16 and a flexible spacer 20 is disposed there between to control motion of the spine, while otherwise leaving the spinal segment mobile. Alternatively, the two anchors can be placed in a patient in combination with a fusion device located between the vertebral bodies.

The spacer 20 and pedicle screws 12 are coupled together by a connecting element 22 which in one embodiment is a flexible member coupled to or passed through the spacer 20 and secured to the heads 24 of the screws 12. Such spacers 20 and flexible members 22 may be similar to those used in the Dynesys® Dynamic Stabilization System available from Zimmer Spine of Minneapolis, Minn. In one embodiment, the spacer 20 may be formed from polycarbonate urethane and the flexible member 22 is a cord that may be formed from polyethylene-terephthalate, although it will be recognized that various other materials suitable for implantation within the human body and for providing stabilization of the spine while maintaining flexibility may be used.

In one embodiment, the anchor 12 is a pedicle screw having a threaded shank 26 configured to be screwed into the pedicle area of a vertebra 14,16. The head 24 of the screw is configured to receive and secure the flexible member 22. In the embodiment shown, the head 24 includes an upwardly open channel 28 formed between upwardly directed arms 30 and extending generally transverse to the longitudinal axis of the shank 26 and having an open end opposite the shank 26 for receiving the flexible member 22 into the channel 28 of the head 24 in a top loading fashion. Accordingly, the channel 28 alleviates the need to thread the flexible member 22 through an eyelet of the head 24 of the anchor 12 after the anchor 12 has been installed into the vertebral body 14, 16 of a patient's spine. The head 24 may have a pair of spaced, generally flat faces 33 for juxtaposition to the spacer 20.

In this embodiment, the head 24 of the pedicle screw 12 has receiving channels, such as recesses 32, provided on oppositely disposed sides of the arms 30 of the head 24 to facilitate screwing the anchor 12 into a vertebra 14,16 of a patient's spine using a tool as described later herein. In one embodiment, the pedicle screw 12 is formed from a titanium alloy, but it will be recognized that various other materials suitable for implantation within the human body and having sufficient strength to be securely attached to the bone and to secure the flexible member 22 may be used. While a uniaxial pedicle screw is shown and described herein, it will be recognized that the anchor 12 may alternatively comprise a hook, a polyaxial pedicle screw, or various other structure suitable to be secured to a vertebral body.

An elongate access member 18 is removably secured to the head 24 of the pedicle screw 12 and is formed substantially from a resilient, flexible material that permits deformation or bending of the access member 18 along its length without transmitting significant force to the pedicle screw 12. For example, the access member 18 may be formed from polymeric material such as nylon, polyethylene, polyurethane, or various other polymeric materials that are biocompatible and provide sufficient flexibility to permit the guides to bend in flexure along their length without transmitting significant force to the pedicle screw 12. In other exemplary embodiments, the access members 18 may be configured as a rigid or a composite structure, comprising a portion formed from a substantially rigid material and a portion comprising a flexible material or wholly of a rigid material.

Figure 2:
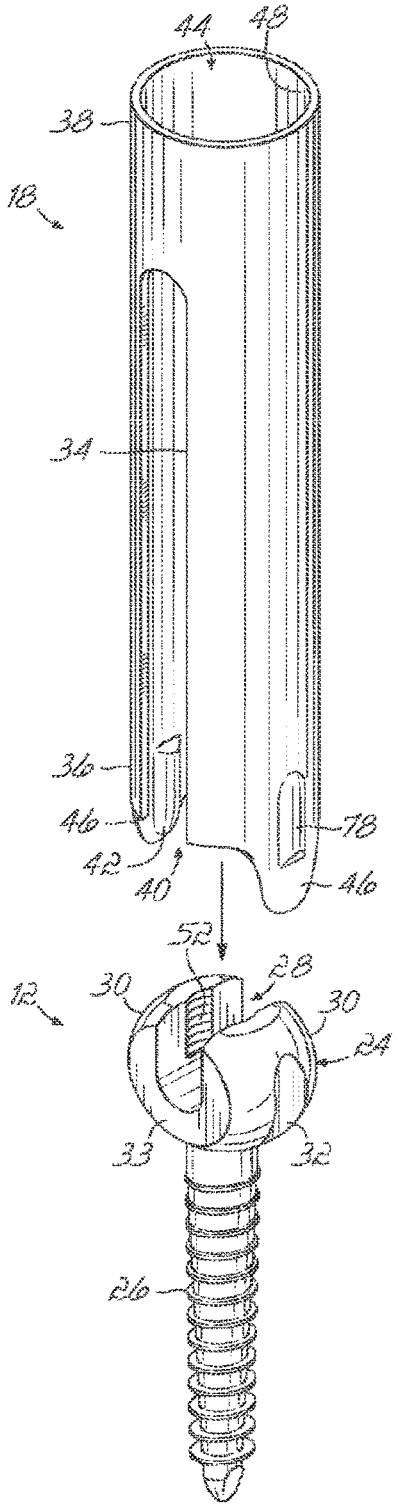
FIG. 2 is a perspective view of the vertebral anchor of FIG. 1 being coupled to an access sleeve according to one aspect of this invention.

In the embodiment shown in FIG. 2, the access member 18 includes a pair of diametrically opposed, longitudinal slots 34 extending from a first, distal end 36 toward a second, proximal end 38 of the access member 18. Each slot 34 has an opening 40 at the first end 36 that is shaped to mate with the head 24 of the pedicle screw 12 such that the slot 34 communicates with the channel 28 formed in the head 24 of the pedicle screw 12. In this arrangement, the longitudinally extending slot 34 may be used to guide the flexible member 22 from the slots 34 of the access member 18, along its length, and into the channel 28 formed in the head 24 of the pedicle screw 12.

In one embodiment, the access member 18 includes mating tabs 42 to mate with the receiving channels or recesses 32 on the head 24 of the pedicle screw 12. In the exemplary embodiment shown, the mating tabs 42 are inwardly directed protrusions. Mating surfaces between the pedicle screw and the access member 18 are configured to provide a mechanical interlock that is sufficient to withstand forces applied to the access member 18 during installation of the pedicle screws 12 into the vertebrae 14,16 and installation of the spacer 20 between adjacent pedicle screws 12. However, the access members 18 may be removed from the heads 24 of the pedicle screws 12, for example, by application of an appropriate force or by manipulating the access member 18 relative to the pedicle screw 12, to cause the mating tabs 42 on the access member 18 to dislodge from the recesses 32 on the head 24 of the pedicle screw 12. The access member 18 may be formed in a molding process in the form of a sleeve having a longitudinally extending cannula 44, and may thereafter be joined to the head 24 of the pedicle screw 12 by mechanically interlocking the sleeve 18 onto the head 24 of the pedicle screw 12 with the mating tabs 42 and receiving channels or recesses 32.

With continued reference to FIGS. 1-2, the sleeve 18 includes an aperture 48 proximate the second end 38 for receiving various components including a fastener 50, such as a set screw, for securing the flexible member 22 to the head 24 of the pedicle screw 12, as will be described more fully below. The aperture 48 leads to the cannula 44 of the access member 18 to provide percutaneous access to the head 24 of the pedicle screw 12.

Longitudinally extending and laterally oriented threads 52 are formed on the inwardly facing surfaces of the arms 30 in the channel 28 of the head 24. The threads 52 are sized for engagement with the fastener 50 when it is desired to secure the flexible member 22 to the head 24 of the pedicle screw 12. In one embodiment, a driver 54 (FIG. 7) or other tool suitable for engaging a socket 56 in a top face of the fastener, or set screw, 50 may be inserted through the cannula 44.

While the fastener 50 has been shown and described herein as comprising a set screw, it will be recognized that various other types of securing members may alternatively be used to secure the flexible member 22 to the head 24 of the anchor 12. Likewise, the sleeve 18 may be configured to accommodate these various other types of fasteners and to percutaneously provide access for them to the anchor 12.

Figure 3:
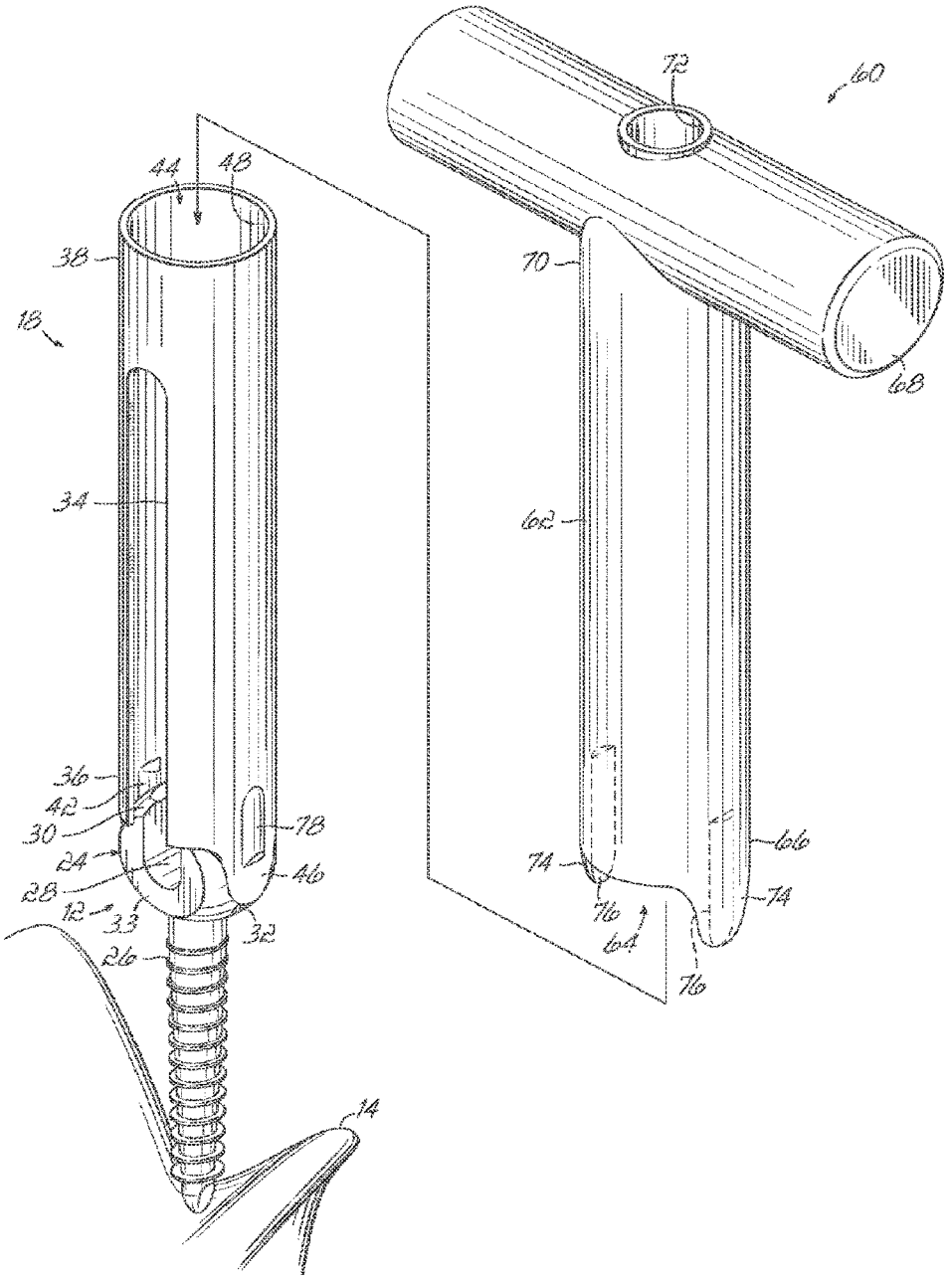
FIG. 3 is a perspective view of the components of FIG. 2 being coupled to a tool according to another aspect of this invention.
Figure 4:
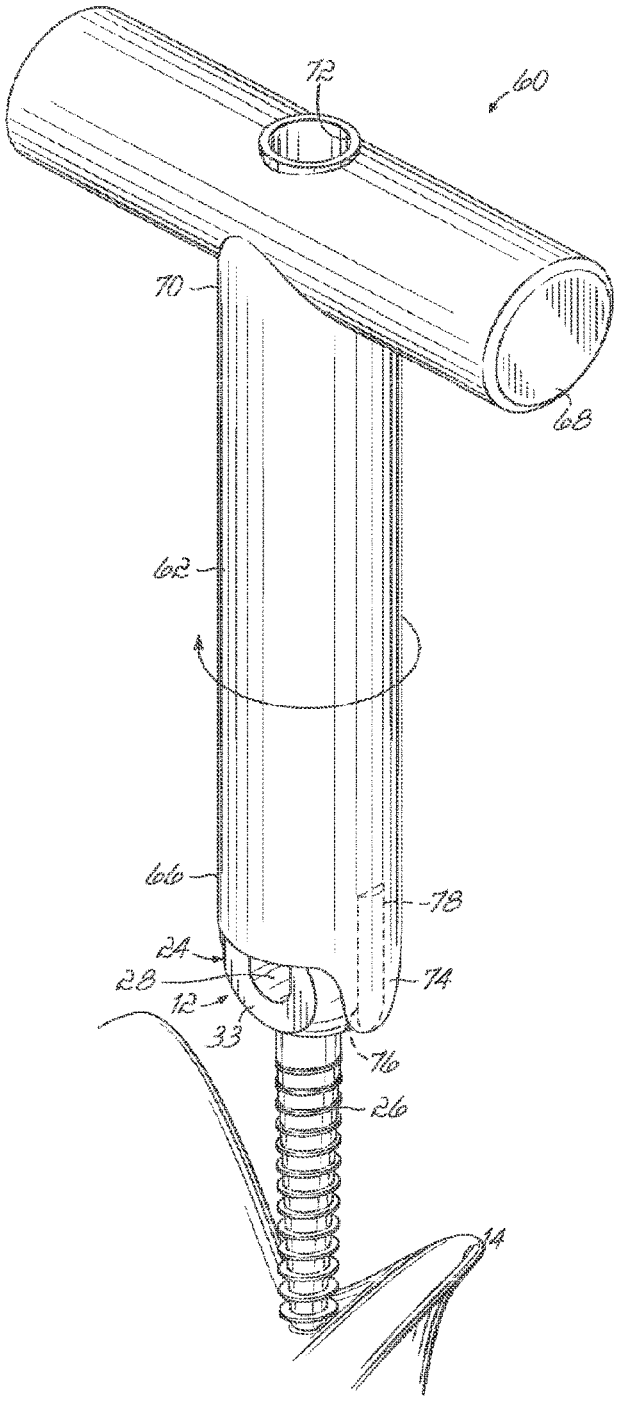
FIG. 4 is a perspective view of the components of FIG. 3 being used to screw a first vertebral anchor into a vertebra of a patient.

Referring now to FIG. 3, use of a tool 60 to install components of the spinal stabilization system 10 to the vertebrae 14,16 of a spine will now be described. Vertebral anchor 12 and sleeve 18 mated together have been inserted through a minimally invasive incision formed in a patient's skin to be threadably secured into the pedicle areas of a vertebra 14,16. The tool 60 in one embodiment as shown includes a tubular member 62 extending longitudinally and defines a central cannula 64 extending from a distal end 66 of the tool 60. The tool 60 includes a handle 68 at the proximal end 70 of the tubular member 62, and the handle 68 and tubular member 62 in combination form a generally T-shaped configuration according to one embodiment of the tool 60. In one embodiment, the T-shaped handle configuration of handle 68 can be incorporated into the sleeve 18. The proximal end 70 of the cannula 64 in the tubular member 62 is accessed through a port 72 in the handle 68 as shown in FIGS. 3 and 4. The port 72 is sized to receive a fastener 50. The handle 68 provides a convenient grip for a surgeon to grasp the tool 60 for manipulation during installation of the spinal stabilization system 10. The distal end 66 of the tubular member 62 includes a pair of diametrically opposed fingers 74 projecting downwardly. Tool receiving channels, such as recesses 76, are formed on an inner face of each finger 74 and extend longitudinally toward the body portion of the tubular member 62. The cannula 64 and tubular member 62 are sized and configured to fit over the access member 18 and pedicle screw 12 combination as shown in FIG. 3.

Referring to FIG. 4, with the tool 60 installed onto and over the access member 18 and pedicle screw 12 in a generally telescopic arrangement, the recesses 76 at the distal end 66 of the tubular member 62 mate with outwardly directed tool mating tabs 78 on the distal end of the access member 18. As a result, the tool 60 is mated with the vertebral anchor 12 and access member 18. The mating interaction of the mating tabs 42, 78 and recesses 32, 76 allow the T-shaped tool 60 to drive the pedicle screw 12 as well as act as an anti-torque instrument. The surgeon rotates the tool 60 mated with the vertebral anchor 12 and access member 18 to screw the vertebral anchor 12 into the vertebra 14,16. The tool 60 can then be uncoupled from the access member 18 by dislodging the tool mating tabs 78 from the recess 76, thereby leaving the access member 18 mounted on the pedicle screw 12 installed on the vertebra 14,16.

Figure 5:
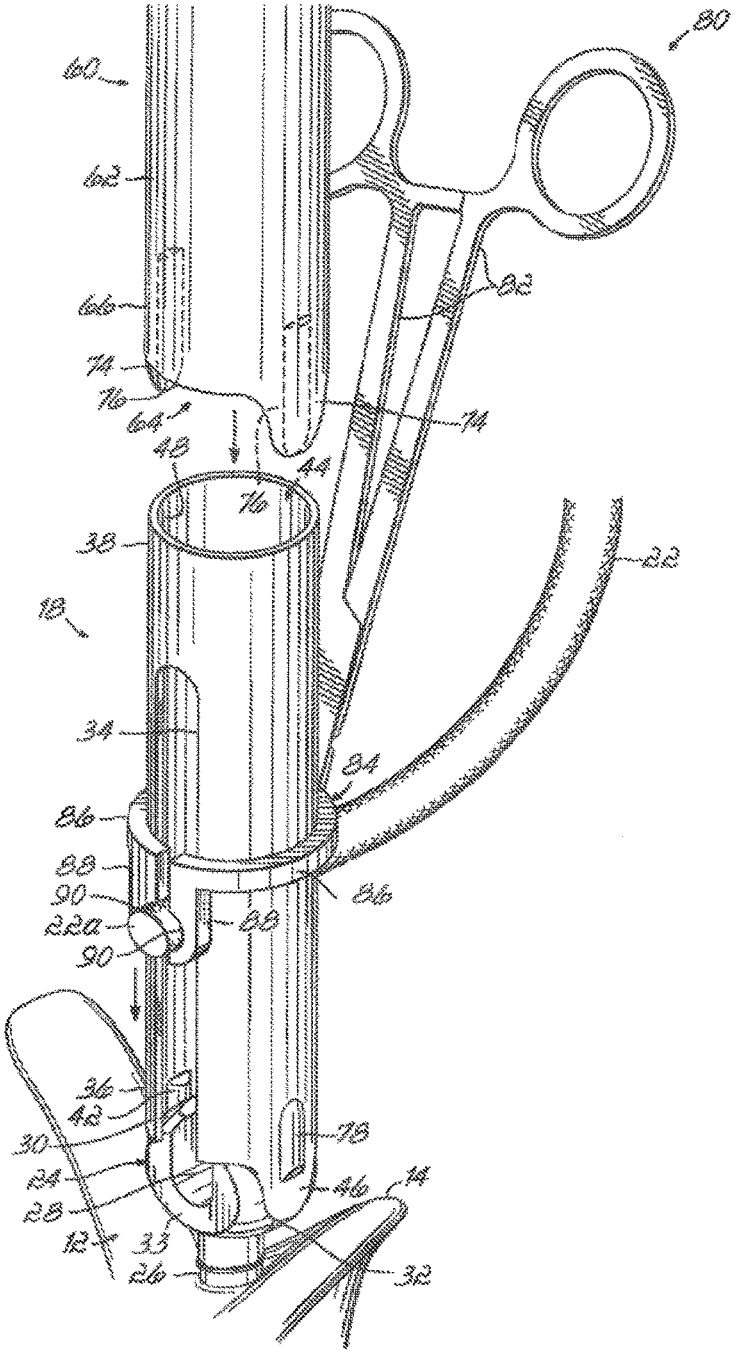
FIG. 5 is a perspective view of a connecting element of a dynamic stabilization system being installed on the first vertebral anchor of FIG. 4.

The above-described description of the installation of the pedicle screw 12 may be performed on each of the pedicle screws 12 utilized in the stabilization system 10 as appropriate. In FIG. 5, the attachment of the connecting member, such as the exemplary flexible member 22 in the form of a flexible cord, to one of the pedicle screws 12 is shown. The pedicle screw 12 installed in the vertebra 14 has the access member 18 mounted thereto as shown in FIG. 5. A terminal end 22a of the connecting element 22 is inserted through the slots 34 of the access member 18 and this is likely performed at a portion of the slots 34 and access member 18 extending from the patient's body and above the incision. A forceps 80 having a pair of elongate handle members 82 pivotally coupled together can be utilized to stabilize and maneuver the flexible member 22 in the access member slots 34. The forceps 80 include cooperating jaws 84, each of which has an arcuate portion 86 and a downwardly depending leg 88 with a notch 90 proximate the distal end of the leg 88 as shown in FIG. 5. In combination, the jaws 84 of the forceps 80 surround the access member 18 and the notches 90 clamp the end 22a of the flexible member 22 projecting through the slot 34. Any excess portion of the flexible member 22 that overhangs the notches 90 may be severed or trimmed as desired.

With the flexible member 22 clamped by the forceps 80 and projecting through the slots 34 in the access member 18 as shown in FIG. 5, the flexible member 22 may be passed through the slots 34 and down to the channel 28 of the pedicle screw 12. The forceps 80 clamped onto the flexible member 22 and around the access member 18 may be utilized to push the flexible member 22 from the slots 34 and into the channel 28. Alternatively, the tubular member 62 of the tool 60 may be used in combination with the forceps 80 to advance the flexible member 22 from the slots 34 downwardly and into the upwardly open channel 28 of the pedicle screw 12 as shown in FIG. 5.

With the flexible member 22 seated in the channel 28 and secured therein by the forceps 80, the fastener or set screw 50 may be percutaneously introduced through the cannula 44 of the access member 18 for securing the flexible member 22 to the pedicle screw 12. A driver 54 or similar tool may be utilized to threadably secure the set screw 50 to the head 24 of the pedicle screw 12 thereby securing the flexible member 22 to the pedicle screw 12. The tubular member 62 and T-shaped tool 60 may continue to be mounted telescopically on the access member 18 and pedicle screw 12 or removed for easier access and installation of the set screw 50.

Figure 6:
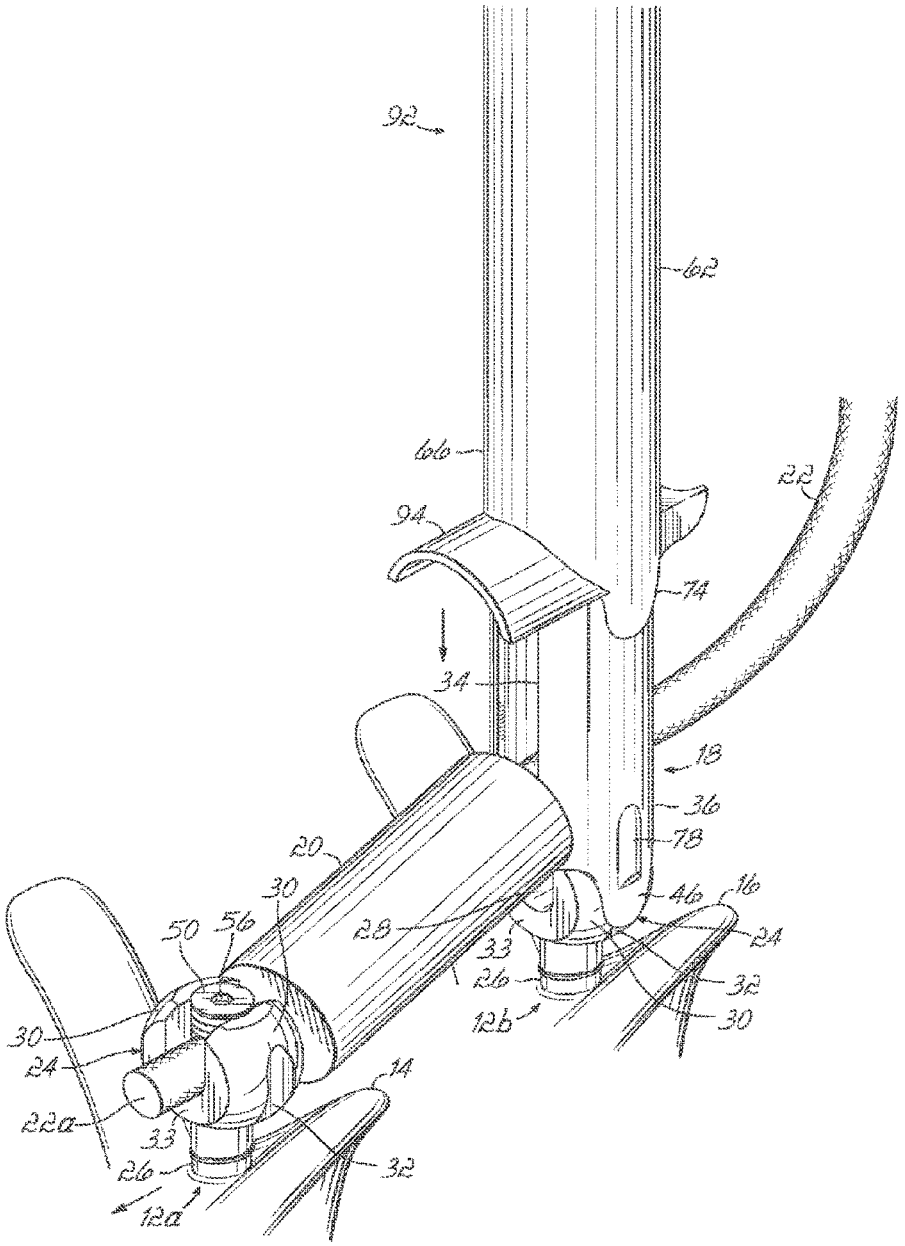
FIG. 6 is a perspective view of the components of the dynamic stabilization system being installed relative to a pair of vertebral anchors installed on respective vertebrae of the patient.
Figure 7:
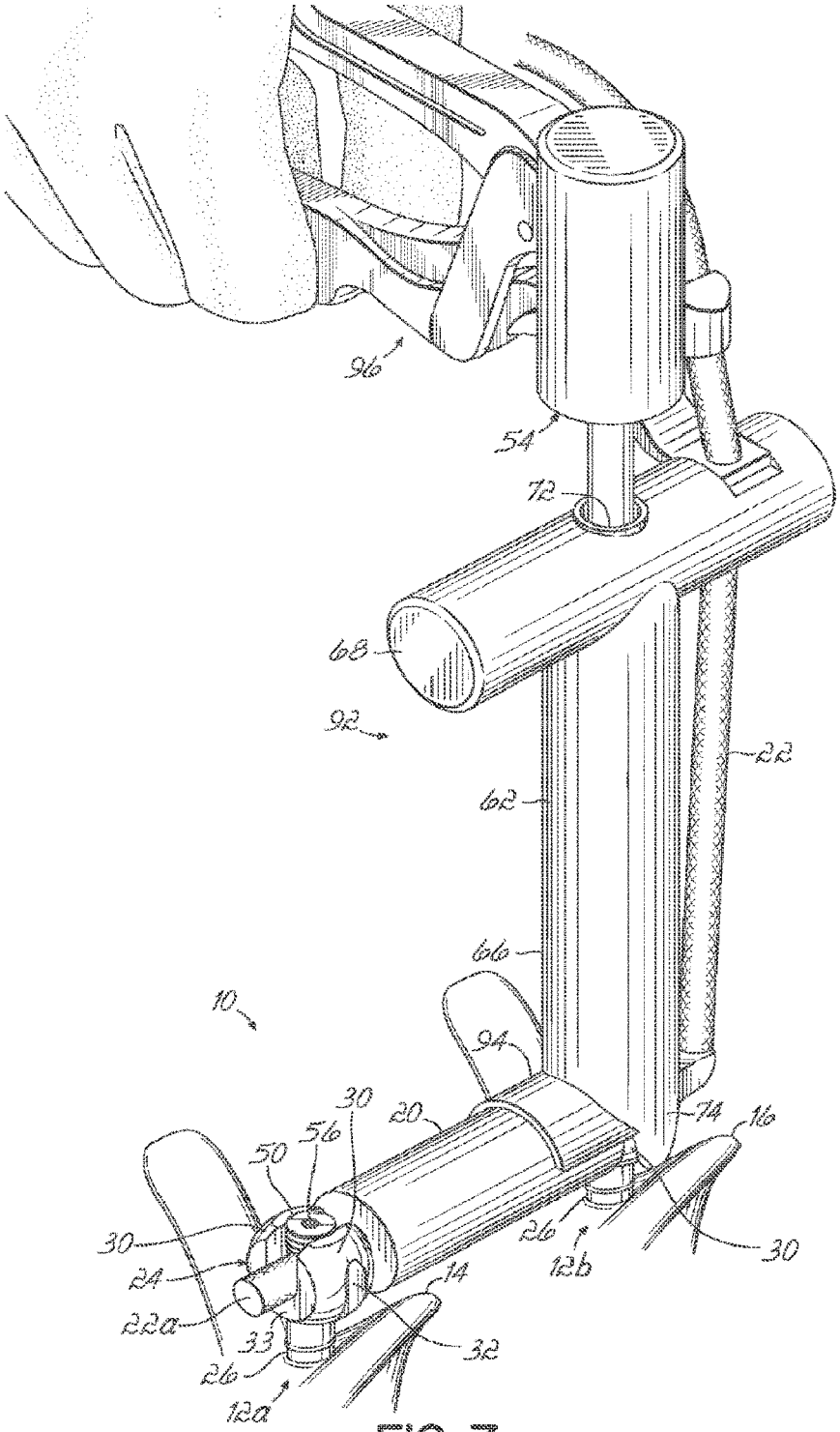
FIG. 7 is a perspective view of the connecting element of the dynamic stabilization system being tensioned between the vertebral anchors and the anchors being distracted during the tensioning process.

Referring to FIGS. 6 and 7, the adjacent pedicle screw 12a has been placed in the associated vertebra 14 with the procedure as previously described. The spacer 20 is then put over the flexible member 22 and slid into contact with the head 24 of the first pedicle screw 12a as shown in FIG. 6. The tool 62 can be used to create distraction between the vertebral anchors 12a, 12b to allow for easier placement of the spacer 20 between the vertebral anchors 12a, 12b. Alternatively, a distractive force can be generated by the placement of the spacer 20 between the vertebral anchors 12a, 12b. As the tool 62 shown in FIG. 6 is forced into engagement with the spacer 20, the spacer 20 then generates a force against the vertebral anchors 12a, 12b thus creating distraction of the vertebrae.

The flexible member 22 is then inserted through the slots 34 of the access member 18 on the second pedicle screw 12b and a connecting element guide tool 92 can be slid over the access member 18 on the second pedicle screw 12b as shown in FIGS. 6 and 7. The cord guide tool 92 is similar to the T-shaped tool 60 previously described in FIGS. 3 and 4 with like reference numerals identifying similar features. The flexible member guide tool 92 also includes at least one arcuate flange 94 projecting generally perpendicularly from the axis of the tubular member 62. The arcuate flange 94 is sized and configured to cradle a portion of the spacer 20 as the tool 92 is pushed downwardly over the access member 18. The arcuate flange 94 contacts the end of the spacer 20 adjacent the second pedicle screw 12b and downward pressure on the tool 92 forces the spacer 20 downwardly and into position between the adjacent pedicle screw heads 24. As the cord guide tool 92 slides downwardly over the access member 18, the arcuate flange 94 translates the spacer 20 downward and outward to create distraction by reacting to the force of the flexible member guide tool 92 and pushing against the access member 18 on the second pedicle screw 12b and the head 24 of the first pedicle screw 12a. Simultaneously, the flexible member 22 advances from the slots 34 of the access member 18 on the second pedicle screw 12b and into the channel 28 of the head 24 of the second pedicle screw 12b.

Advantageously, this invention utilizes the tools and spacer to create distraction between the pedicle screw heads 24 and avoids threading the flexible member 22 through an eyelet in the head of the pedicle screw and any over distraction caused by the thickness of the flexible member when pulled into position.

Once the spacer 20 is positioned between the pedicle screw heads 24 and the flexible member 22 is seated in the channel 28 of the second pedicle screw 12b, the flexible member 22 may be tensioned utilizing a tensioning tool 96 as shown in FIG. 7. After the flexible member 22 is appropriately tensioned, the set screw 50 may be passed through the port 70 in the handle 68 of the cord guide tool 92 and seated in the channel 28 of the pedicle screw head 24. The driver 54 is then utilized through the cannula 64 of the tool 92 and the access member 18 to mate with the set screw 50 and rotate the set screw 50 into secure engagement in the channel 28 and thereby clamp the tensioned flexible member 22. The driver 54, cord guide tool 92, access member 18 and tensioning tool 96 may then be removed from the patient and the flexible member 22 trimmed to length. Alternatively, if a multi-level spinal dynamic stabilization system 10 is to be installed, the process is repeated on subsequent vertebrae as appropriate and the incision closed to complete the installation.

While this invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of the general inventive concept.

What is claimed is:

[1. A method of installing a spinal stabilization construct, comprising:

installing first and second vertebral anchors onto first and second vertebrae, respectively, each vertebral anchor having an upwardly open channel adapted to receive a flexible connecting element extending between the first and second vertebrae;

mounting first and second access members onto the first and second vertebral anchors, respectively, each access member having a cannula to provide access to the channel of the respective vertebral anchor;

inserting the connecting element through a slot in the first access member;

advancing the flexible connecting element from the slot in the first access member into the channel of the first vertebral anchor;

securing the flexible connecting element to the channel of the first vertebral anchor with a first fastener;

positioning a spacer on the connecting element adjacent the first vertebral anchor;

inserting the flexible connecting element through a slot in the second access member;

translating a tool along an exterior of the second access member without rotation to advance the flexible connecting element along the slot in the second access member into the channel in the second vertebral anchor;

positioning the spacer between the vertebral anchors; and securing the flexible connecting element to the channel of the second vertebral anchor with a second fastener.]

[2. The method of claim 1, wherein positioning the spacer between the vertebral anchors includes:

pushing the spacer into position between the vertebral anchors with the tool.]

[3. The method of claim 2, wherein the tool includes a lateral portion extending transverse to a longitudinal axis of the tool for contacting the spacer.]

[4. The method of claim 3, wherein the lateral portion is a flange including an arcuate surface.]

[5. The method of claim 4, wherein the arcuate surface contacts an outer surface of the spacer.]

[6. The method of claim 1, wherein the tool is a tubular member slidably disposed around the second access member.]

[7. The method of claim 1, further comprising:

tensioning the connecting element after securing the flexible connecting element to the channel of the first vertebral anchor and prior to securing the flexible connecting element to the channel of the second vertebral anchor.]

[8. The method of claim 1, further comprising:

distracting the first and second vertebrae during positioning of the spacer between the vertebral anchors.]

[9. The method of claim 1, wherein securing the flexible connecting element to the channel of the first vertebral anchor with the first fastener includes passing the first fastener through the first access member percutaneously to the first vertebral anchor, and securing the flexible connecting element to the channel of the second vertebral anchor with the second fastener includes passing the second fastener through the second access member percutaneously to the second vertebral anchor.]

*10. A system for stabilizing a patient's spine comprising:*

*a plurality of vertebral anchors adapted to be anchored to a plurality of vertebrae, each vertebral anchor having an upwardly open channel defined between upwardly directed arms;*

*a flexible cord adapted to extend between the vertebral anchors and be seated in the channels;*

*a plurality of fasteners adapted to be mated with the upwardly open channel in each of the plurality of vertebral anchors to secure the cord in the plurality of vertebral anchors;*

*a plurality of access members configured to be coupled to the plurality of vertebral anchors, respectively;*

*a cord guide tool engageable with a first one of the plurality of vertebral anchors by slideably engaging and translating along an exterior of a first access member of the plurality of access members coupled to the first one of the plurality of vertebral anchors without rotation, the cord guide tool including a lumen extending therethrough in communication with the upwardly open channel of the first vertebral anchor;*

*a tensioning tool engageable with a proximal end region of the cord guide tool; and*

*a driver engageable with a first one of the plurality of fasteners to secure the first fastener in the upwardly open channel of the first vertebral anchor through the lumen of the cord guide tool.*

*11. The system of claim 10, wherein the cord guide tool includes a handle and an elongate shaft extending distally from the handle.*

*12. The system of claim 11, wherein the tensioning tool is configured to engage the handle of the cord guide tool.*

*13. The system of claim 11, wherein the handle of the cord guide tool includes a port providing access to the lumen of the cord guide tool.*

*14. The system of claim 13, wherein the handle of the cord guide tool is T-shaped.*

*15. The system of claim 10, wherein the tensioning tool includes a handle portion having first and second actuatable arms configured to be gripped by a hand of a user.*

* * * * *